US006969591B2

(12) United States Patent
Hara

(10) Patent No.: US 6,969,591 B2
(45) Date of Patent: Nov. 29, 2005

(54) METHOD FOR DIAGNOSING NEPHROPATHY

(75) Inventor: Masanori Hara, 31-30 Sakaihigashi 5-chome, Niigata-shi, Niigata 950-2041 (JP)

(73) Assignee: Masanori Hara, Niigata (JP)

( * ) Notice: Subject to any disclaimer, the term of this patent is extended or adjusted under 35 U.S.C. 154(b) by 0 days.

(21) Appl. No.: 10/415,264

(22) PCT Filed: Sep. 28, 2001

(86) PCT No.: PCT/JP01/08512

§ 371 (c)(1),
(2), (4) Date: Oct. 10, 2003

(87) PCT Pub. No.: WO02/37099

PCT Pub. Date: May 10, 2002

(65) Prior Publication Data

US 2004/0058395 A1 Mar. 25, 2004

(30) Foreign Application Priority Data

Oct. 27, 2000 (JP) ........................ 2000-329102

(51) Int. Cl.$^7$ .................... G01N 33/53; B01D 50/00
(52) U.S. Cl. ................ 435/7.1; 435/174; 435/287.1; 435/287.7; 435/288.7; 422/161; 422/164; 422/169; 422/172
(58) Field of Search ............ 435/4, 7.1, 7.92, 435/7.93, 7.94, 7.95, 174, 287.1; 436/518, 528, 535, 538, 287.7, 288.7; 422/161, 164, 169, 172

(56) References Cited

U.S. PATENT DOCUMENTS

| | | | | |
|---|---|---|---|---|
| 4,861,711 A | | 8/1989 | Friesen et al. ................ 436/7 |
| 5,246,835 A | * | 9/1993 | Suzuki et al. .............. 435/7.95 |
| 5,654,158 A | * | 8/1997 | McDonald .................. 435/7.1 |
| 5,707,818 A | * | 1/1998 | Chudzik et al. ........... 435/7.93 |
| 6,207,811 B1 | * | 3/2001 | Tryggvason et al. ....... 536/23.1 |
| 6,395,882 B1 | * | 5/2002 | Rosen et al. ................ 530/395 |
| 6,673,629 B2 | * | 1/2004 | Yoshimura et al. ......... 436/518 |

FOREIGN PATENT DOCUMENTS

| | | |
|---|---|---|
| JP | 61-145459 | 7/1986 |
| JP | 6-11507 | 1/1994 |
| WO | WO 97/08549 | 3/1997 |
| WO | WO 00/52023 | 9/2000 |

OTHER PUBLICATIONS

Hara et al., Immunohistochemical and urinary markers of podocyte injury. 1998. Pediatric Nephrology, 12:43–48.*

Hara et al., Urinary excretion of podocytes reflects disease activity in children with glomerulonephritis. 1998. American Journal of Nehprology, 18:35–41.*

International Search Report for PCT/JP01/08512.

* cited by examiner

*Primary Examiner*—Long V. Le
*Assistant Examiner*—Melanie J. Yu
(74) *Attorney, Agent, or Firm*—Kilyk & Bowersox, P.L.L.C.

(57) ABSTRACT

Means of conveniently examining nephropathy; and a method of assaying substance(s) in association with nephropathy (for example, podocalyxin and/or nephrin) in the urine to be used in the above means. The above assay method can be provided by releasing proteins in association with nephropathy, which exist on the surface of podocytes, from the cell surface and thus assaying the substances existing on the cell surface and/or free substances contained in the urine.

7 Claims, 1 Drawing Sheet

METHOD FOR DIAGNOSING NEPHROPATHY

This application is a National Stage entry of earlier filed International Application No. PCT/JP01/08512 filed Sep. 28, 2001.

TECHNICAL FIELD

The present invention relates to a method for detecting or assaying podocalyxin and/or nephrin in a biological specimen, in particular, urine, a means for examining nephropathy, and a reagent (kit) for assaying podocalyxin and/or nephrin.

BACKGROUND ART

It is known that a glomerulal podocyte variously changes in the nephritis crisis. In a congenital nephrotic syndrome patient, for example, it was demonstrated that podocyte nephrin is not expressed, and the importance of podocyte, in particular, that of nephrin has been elucidated in the appearance of albuminurea. Urine sediments contain various components such as ones derived from the kidney, ones contaminated from the urinary tract, and ones precipitated in urine. It is important to examine the kind and amount of urinary sediments for discriminating kidney and urinary tract diseases and knowing their degree. These are usually carried out by the staining followed by the microscopy. It is described that it is useful to observe a podocyte with a microscope in order to detect, as a marker, podocalyxin that is a glycoprotein present on the surface of a kidney podocyte for understanding the condition of nephropathy. (Amer. J. Nephrol. 18, 35–41 (1998)).

However, these assays were carried out by the staining, in particular, the fluorescence-labelled immunostaining using a monoclonal antibody, followed by the microscopy. As tests are carried out by the microscopic examination of each specimen one by one in these methods, procedures were laborious and it was not easy to assay many specimens.

On the other hand, Japan Patent no.2932837 describing a method for assaying human podocalyxin by the enzyme immunoassay or immunoprecipitation only disclosed examples of a method for immunologically assaying human podocalyxin, but did not disclose a method for assaying practical clinical specimens, a result of it, or its clinical utility.

DISCLOSURE OF THE INVENTION

The purpose of the present invention is to provide a means for simply examining the nephropathy, and to provide a method for assaying a substance observed in association with the nephropathy using the examination means, for example, podocalyxin and/or nephrin in urine.

By a research, inventors found a method for assaying substances (e.g., podocalyxin, nephrin) that is/are observed in association with nephropathy and present on the surface, for example, of podocyte, membrane protein, and cells that constitute uriniferous tubule and/or renal glomerular and are contained in urine (urinary residents) are released into urine by the treatment that releases podocalyxin and nephrin from the surface of cells. The inventors found that a method for assaying these substances observed in association with nephropathy is useful for examining the nephropathy, and completed this patent.

The present invention provides:
1. A method for assaying substance(s) in urine, wherein the method is characterized by introducing the substance(s) contained in urine sediments into an assay system.
2. A method for assaying substance(s) in urine according to foregoing paragraph 1, wherein the method is characterized by introducing, into an assay system, the substance(s) present in cells that constitute the uriniferous tubule and/or renal glomerular contained in urine.
3. An assay method according to foregoing paragraph 1 or 2, wherein introducing the substance(s) into an assay system is characterized by converting the substance(s) in urine to one(s) in a free state.
4. An assay method according to foregoing paragraph 1, 2 or 3, wherein converting the substance(s) in urine to one(s) in a free substance is characterized by treating the specimen with a surfactant.
5. An assay method according to foregoing paragraph 1, 2, 3 or 4, wherein the objective substance(s) in urine is/are substance(s) present on the surface of cells contained in urine and/or in a free state in urine.
6. An assay method according to foregoing paragraph 1, 2, 3, 4 or 5, wherein the objective substance(s) is/are one or more selected from a group consisting of podocyte, tubule epithelial cell, membrane protein, and podocalyxin and nephrin present in a podocyte.
7. An assay method according to foregoing paragraph 6, wherein podocalyxin and nephrin are simultaneously assayed in the method.
8. An assay method according to foregoing paragraph 6 or 7, wherein podocalyxin is assayed by the immunochromatography using an anti-podocalyxin antibody or a fraction thereof labelled with a substance or particle whose signal can be directly or indirectly detected.
9. An assay method according to foregoing paragraph 6 or 7, wherein nephrin is assayed by immunochromatography using an anti-nephrin antibody or a fraction thereof labeled with a substance or particle whose signal can be directly or indirectly detected.
10. A means for examining nephropathy using an assay method described in foregoing paragraph 1, 2, 3, 4, 5, 6, 7, 8 or 9.
11. An assay reagent for an assay method described in foregoing paragraph 1, 2, 3, 4, 5, 6, 7, 8 or 9.
12. An assay kit consisting of a treatment reagent for introducing substance(s) present on the surface of cells present in urine into an assay system and an assay reagent described in foregoing paragraph 11 for immunologically assaying substance(s) in urine.

Figure 1:
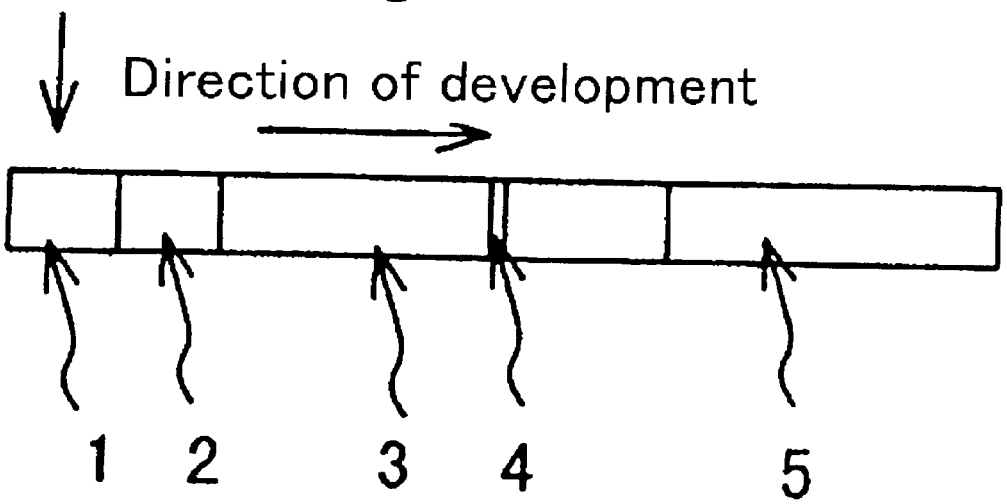
FIG. 1 illustrates a flat view of an immunochromatograph.
Figure 2:
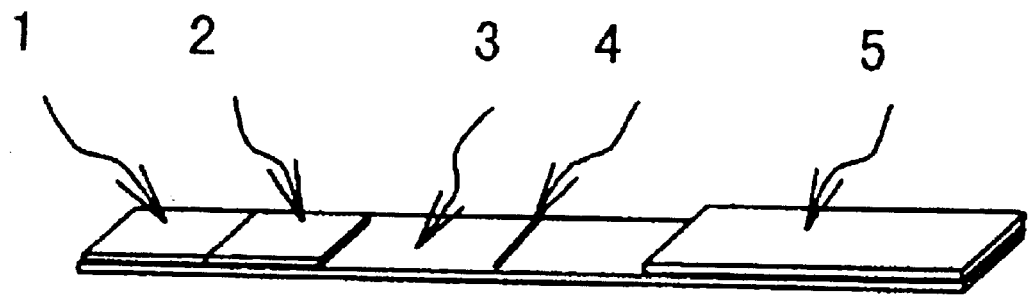
FIGS. 2 and 3 illustrate a cubic diagram of an immunochromatograph.

The following parts can be seen in FIGS. 1 and 2: 1, specimen-adding pad (specimen-adding site); 2, labelling pad (anti-podocalyxin antibody-labelled colored particle-carrying part); 3, development membrane; 4, catching site (anti-podocalyxin antibody or wheat embryo lectin fixing part); 5, absorption pad. The following parts can be seen in FIG. 3: 6, specimen-adding pad (specimen-adding site); 7, labelling pad (anti-podocalyxin antibody-labelled colored particle and anti-nephrin antibody-labelled colored particle-carrying part); 8, development membrane; 9, catching site (anti-podocalyxin antibody-fixing part); 10, catching site (anti-nephrin antibody-fixing part); 11, absorption pad.

BEST MODE FOR CARRYING OUT THE INVENTION

The present invention relates to an assay of substances that are observed in association with nephropathy as a means for examining the nephropathy, and has the following properties:

Substances to be assayed according to the present invention can be observed in association with nephropathy and are contained in urine. In particular, the substances (e.g., podocalyxin, nephrin) are present on the surface of substances which are contained in urinary sediments, for example, cells for constituting podocytes, membrane protein, uriniferous tubule and renal glomerular. The assay method according to the present invention includes a treatment step of converting those substances to a free state, wherein the treatment step includes a surfactant-treatment step. Those substances are released from the surface of the cells by the surfactant treatment, so that those substances are present in urine specimen in a free state.

Assaying podocalyxin and/or nephrin contained in urine can be performed by a well-known immunological method, preferably by a rapid and simple assay method, by the immunochromatography using an antibody or a fraction thereof labelled with a substance or particle whose signal can be at least directly or indirectly detected.

The present invention also provides a means and reagents for examining the nephropathy using the above immunochromatography, a pretreatment reagent for releasing substance(s) (e.g., podocalyxin, nephrin) from the surface of cells contained in urine, and a podocalyxin assay kit that comprises the above immunoassay reagent and the pretreatment reagent.

One of means for solving the subjects according to the present invention is a method for assaying substance(s) (e.g., podocalyxin, nephrin) present on the surface of cells contained in urine specimen and/or substance(s) present in urine specimen in a free state, after a treatment step enough to release substance(s) from the surface of cells contained in urine. Making substances (e.g., podocalyxin, nephrin) present on the surface of cells contained in urine be one(s) in a free state allows it/them to present at a substantially even concentration throughout urine specimen. Making podocalyxin and/or nephrin be present evenly throughout urine also permits assaying podocalyxin and/or nephrin present on the surface of cells together with podocalyxin and/or nephrin present ab initio in a free state in urine.

Treatment of Specimen for Assay

Urine specimens for the present invention include urine per se and urine sediments and supernatant obtained by centifuging urine. The assay method according to the present invention permits not only directly assaying substance(s) without treating urine specimen but also assaying substance(s) (e.g., podocalyxin, nephrin) present on the surface of cells in fraction of urine sediments obtained by centrifuging urine. An appropriate volume of urine to collect for the assay is 50–100 mL or so and 50 mL is enough for the assay. The volume can be reduced depending on the concentration of podocalyxin and/or nephrin contained in the specimen.

Addition of Surfactant

The present invention includes a step of treating a specimen with a surfactant as a means for converting substance(s) (e.g., podocalyxin, nephrin) present on the surface of cells contained in urine to one(s) in a free state. Any kind and concentration of the surfactant can be used as long as the surfactant allows substance(s) (e.g., podocalyxin and/or nephrin) present on the surface of cells in urine to one(s) in a free state can be used and it is preferable that they are ones that do not disturb the immunoassay of podocalyxin and/or nephrin.

Although Triton X-100 is exemplified as a non-ionic surfactant used in the present invention, other surfactant can also be used. Persons skilled in the art can compare effects of surfactants by simply repeating an experiment based on the results disclosed in the present invention to find out a surfactant effective for releasing and assaying podocalyxin and/or nephrin present on the surface of cells contained in urine. Surfactants that can be used include non-ionic surfactants, cationic surfactants, anionic surfactants, amphoteric surfactants and glycosides.

In addition, using two or more kinds of surfactants at the same time permits more surely solubilizing or dispersing substance(s) and enhancing a homogenization effect.

Considering the degree of the release of podocalyxin and/or nephrin, a surfactant can be added in an appropriate amount, in general 0.02–5% (w/v), preferably 0.1–2% (w/v), more preferably 0.2–1% (w/v).

It is preferable to find optimal conditions treatment (e.g., temperature, time) which can be found by simple repeated experiments. Usually, a preferred temperature is 10–40° C., and a preferred time is several seconds to several minutes or so. It is also possible to add a surfactant as the pretreatment to release substance(s) (e.g., podocalyxin, nephrin) present on the surface of cells to prepare a homogenous specimen.

Releasing Agent other than Surfactant

Releasing agents other than surfactants include urea, chaotropic salts (e.g. thiocyanate, periodate and perchlorate), and guanidine hydrochloride, which are well known. These releasing agents can be used singly or together with a surfactant.

Method for Assaying Podocalyxin

Methods for assaying podocalyxin present on the surface of cells contained in urine and/or free podocalyxin contained in urine include the immunochromatography using an anti-podocalyxin antibody or a fraction thereof labelled with a substance or particle whose signal can be at least directly or indirectly detected.

Method for Assaying Nephrin

Methods for assaying nephrin present on the surface of cells contained in urine and/or free nephrin contained in urine include immunochromatography using an anti-nephrin antibody or a fraction thereof labeled with a substance or particle whose signal can be at least directly or indirectly detected in a manner same as that of podocalyxin.

The immunochromatography is usually carried out by using a particle-labelled antibody prepared by making fine particles for labelling such as gold colloid, colored and fluorescent latex particle absorb the antibody. The labelled particles are usually used by maintaining on a porous carrier usually called "labelled pad".

Figure 3:
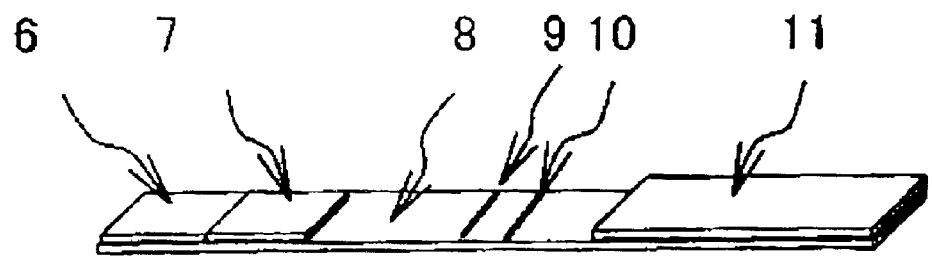

On the other hand, it is also possible to assay objective substance(s) by migrating a complex formed from a labelling particle and an objective substance in a membrane by the capillary phenomenon, with fixing a trapping ligand onto a part of a porous carrier such as nitrocellulose membrane, with reacting a specimen with the above labelling particles, trapping the labelling particles to the capturing ligand, followed by observing/assaying the degree of trapping of the labelled particles. This method permits a simple and rapid assay, and is hence useful for the bed-side examination. Using the immunochromatography for assaying podocalyxin or nephrin in urine permits simply and rapidly examining the nephropathy, and thus is very useful for the clinical diagnosis. Assaying podocalyxin and/or nephrin by the immunochromatography together with the usual examinations of sugar and protein permits more surely examining the nephropathy, for example in urine examination in the medical examination for school children. Maintaining a labelled anti-podocalyxin antibody and a labelled anti-nephrin antibody on the same carrier permits simultaneously assaying podocalyxin and nephrin (FIG. 3).

EXAMPLES

Although examples are provided below for further description, the scope of the present invention is not limited by them.

Example 1

Preparation of Immunochromatograph for Assaying Podocalyxin

Anti-human podocalyxin monoclonal antibody was dissolved in a phosphate buffer (pH7.2) so as to give a concentration of 0.1 mg/mL solution. A commercially available colored latex (particle size, 0.3 μm; Bangs Laboratories, Inc.) was added to the solution, and the obtained mixture was left at 37° C. for 3 h, and the resultant mixture was centrifuged to give a labelled latex, which was twice washed with a buffer containing 3% bovine serum albumin and was maintained on a commercially available conjugate pad (Whatman Co.) to give a labelled pad. On the other hand, a trapping ligand was prepared with 2.0 mg/mL wheat germ agglutinin (WGA) in a line having a width of 0.5 mm drawn with a blotter (Bio-DotLaboratories, Inc.) on a nitrocellulose membrane having a pore size of 0.8 μm. Thus prepared membrane was blocked with a buffer containing 1% bovine serum albumin and dried to give an immunochromatograph for assaying podocalyxin as illustrated in FIGS. 2 and 3.

Pretreatment of Urine Specimen 50 mL of urine specimen was mixed using a vortex mixer, left for 30 min, and centrifuged at 500×g for 5 min to give urine sediments. 0.2 mL of saline containing 1% Triton X-100 was added to the urine sediment fraction, and the obtained mixture was mixed using a vortex mixer for 30 sec for extraction with adequately dispersing the sediments. The dispersed specimen was directly subjected to the above immunochromatograph for assay.

Control

The same urine specimen as one pretreated as described above was centrifuged in the same way to give urine sediments, which were immuno-stained with an FITC-labelled anti-human podocalyxin monoclonal antibody to observe podocytes under a microscope.

Result of Assay

Results of assay by the method according to the present invention and results of observation after the fluorescent immunological staining of ten urine specimens are summarized in Table 1. With respect to all ten specimens, results of assay by the method according to the present invention and results of observation after the fluorescent immunological staining coincided. It took about 3 hours to examine all the pretreated urine specimens by the microscopy, while it took only about 15 min to examine all the pretreated urine specimens by the method according to the present invention.

TABLE 1

Results of assay of podocalyxin

| Urine specimen | Method according to present invention | Microscopy |
| --- | --- | --- |
| 1 | + | + |
| 2 | ++ | ++ |
| 3 | − | − |
| 4 | ++ | ++ |
| 5 | + | + |
| 6 | − | − |
| 7 | − | − |
| 8 | + | + |
| 9 | − | − |
| 10 | ++ | ++ |

Example 2

Preparation of Immunochromatograph for Assaying Podocalyxin and Nephrin

Anti-human podocalyxin monoclonal antibody and anti-human nephrin monoclonal antibody were treated in a manner same as that of Example 1 to prepare an immunochromatograph for assaying podocalyxin and nephrin (see FIG. 3).

Treatment of urine according to the present invention and control treatment were carried out in a manner same as Example 1.

Result of Assay

Ten urine specimens were assayed by the method according to the present invention and by observing the same specimens by the fluorescence immunostaining, giving the same results for both methods with respect to all ten specimens (see Table 2).

TABLE 2

Result of assay of podocalyxin and nephrin

| | Podocalyxin | | Nephrin | |
| --- | --- | --- | --- | --- |
| Urine specimen | Method according to the present invention | Microscopy | Method according to the present invention | Microscopy |
| 11 | ++ | ++ | ++ | ++ |
| 12 | + | + | + | + |
| 13 | + | + | + | + |
| 14 | + | + | + | + |
| 15 | − | − | − | − |
| 16 | ++ | ++ | ++ | ++ |
| 17 | − | − | − | − |
| 18 | + | + | + | + |
| 19 | − | − | + | + |
| 20 | ++ | ++ | ++ | ++ |

INDUSTRIAL APPLICABILITY

The method according to the present invention for assaying substance(s) (e.g., podocalyxin and/or nephrin) present in a free and/or bound state in urine by releasing the substance(s) present on the surface of podocytes observed in association with the nephropathy from the surface of the cells permits simply and rapidly examining a urine specimen, and is hence useful for diagnosing the nephropathy.

What is claimed is:

1. A method of assaying a urine sample to determine the presence of at least one substance of interest from sediments of the urine sample and/or from the surface of cells or membranes contained in the urine sample, the method comprising the steps of:

treating the urine sample with a surfactant to convert the at least one substance of interest present in sediments of the urine sample and/or on the surface of cells or membranes contained in the urine sample into a free state in the urine sample and then determine the presence of the at least one substance of interest in the free state in the urine sample wherein the at least one substance of interest is a substance that is present on the surface of podocytes, and wherein the at least one substance of interest is podocalyxin and/or nephrin.

2. A method of assaying a urine sample to determine the presence of at least one substance of interest from sediments of the urine sample and/or from the surface of cells or membranes contained in the urine sample, the method comprising the steps of treating the urine sample with a surfactant to convert the at least one substance of interest present in sediments of the urine sample and/or on the surface of cells or membranes contained in the urine sample into a free state in the urine sample, and then determining the presence of the at least one substance of interest in the free state in the urine sample wherein the at least one substance of interest is podocalyxin and/or nephrin.

3. The method of claim 2 wherein the presence of podocalyxin and nephrin are simultaneously determined.

4. The method of claim 2 wherein the substance of interest is podocalyxin and wherein the step of determining the presence of podocalyxin in the free state in the urine sample is carried out by immunochromatography using a labeled anti-podocalyxin antibody or a labeled anti-podocalyxin antibody fragment.

5. The method of claim 2 wherein the substance of interest is nephrin and wherein the step of determining the presence of nephrin in the free state in the urine sample is carried out by immunochromatography using a labeled anti-nephrin antibody or a labeled anti-nephrin antibody fragment.

6. A method of diagnosing nephropathy comprising carrying out the method of assaying a urine sample according to claim 1, wherein a positive determination of the presence of the substance of interest in the urine sample indicates nephropathy.

7. A method of diagnosing nephropathy comprising carrying out the method of assaying a urine sample according to claim 2 wherein a positive determination of the presence of podocalyxin or nephrin in the urine sample indicates nephropathy.

* * * * *

UNITED STATES PATENT AND TRADEMARK OFFICE
CERTIFICATE OF CORRECTION

PATENT NO.   : 6,969,591 B2
DATED        : November 29, 2005
INVENTOR(S)  : Hara It is certified that error appears in the above-identified patent and that said Letters Patent is hereby corrected as shown below:

Column 6,
Lines 61-67, change "state in the urine sample and then determine the presence of the at least one substance of interest in the free state in the urine sample wherein the at least one substance of interest is a substance that is present on the surface of podocytes, and wherein the at" to read -- state in the urine sample wherein the at least one substance of interest is a substance that is present on the surface of podocytes, and then determining the presence of the at least one substance of interest in the free state in the urine sample and wherein the at --.

Signed and Sealed this

Thirty-first Day of January, 2006

JON W. DUDAS
*Director of the United States Patent and Trademark Office*